(12) United States Patent
Clement et al.

(10) Patent No.: US 6,277,111 B1
(45) Date of Patent: Aug. 21, 2001

(54) DEPILATION

(75) Inventors: Robert Marc Clement; Michael N. Kiernan, both of Swansea (GB)

(73) Assignee: ICN Photonics Limited

( * ) Notice: Subject to any disclaimer, the term of this patent is extended or adjusted under 35 U.S.C. 154(b) by 0 days.

(21) Appl. No.: 09/345,144

(22) Filed: Jun. 30, 1999

Related U.S. Application Data

(63) Continuation-in-part of application No. 08/972,416, filed on Nov. 18, 1997, which is a continuation-in-part of application No. PCT/GB94/02682, filed on Dec. 7, 1994.

(51) Int. Cl.[7] .................................................. A61B 18/18

(52) U.S. Cl. .................................... 606/9; 606/3; 606/10; 606/11; 606/13; 606/127; 606/131; 607/88; 607/89; 128/898

(58) Field of Search .................................. 606/3, 4, 9, 13, 606/10, 15, 44, 222, 127, 131; 607/88–91; 128/898

(56) References Cited

U.S. PATENT DOCUMENTS

| | | | |
|---|---|---|---|
| 5,226,907 | * | 7/1993 | Tankovich ............................ 606/133 |
| 5,630,811 | * | 5/1997 | Miller ...................................... 606/9 |
| 5,647,866 | * | 7/1997 | Zaias et al. ............................. 606/9 |
| 5,735,844 | * | 4/1998 | Anderson et al. ...................... 606/9 |
| 5,836,938 | * | 11/1998 | Slatkine ................................. 606/9 |
| 5,879,346 | * | 3/1999 | Waldman et al. ...................... 606/9 |

* cited by examiner

*Primary Examiner*—Linda C. M. Dvorak
*Assistant Examiner*—Ahmed Farah
(74) *Attorney, Agent, or Firm*—Robert D. Fish; Fish & Associates, LLP

(57) ABSTRACT

Mammalian hair is depilated using a laser source capable of emitting pulse radiation, each pulse having a duration of 1 microsecond to 1 millisecond, and having a wavelength in the range of 600 to 1500 nanometers. The radiation exposure dose is preferably between 2 and 25 J/cm$^2$. A selected area of a subject's skin is irradiated by the pulsed radiation, the area having a plurality of irradiation zones. The laser source is successively pulsed so as to irradiate successive zones of the treatment area with the radiation, so as to destroy subdermal biological material associated with hair growth.

17 Claims, 1 Drawing Sheet

FIG. 1
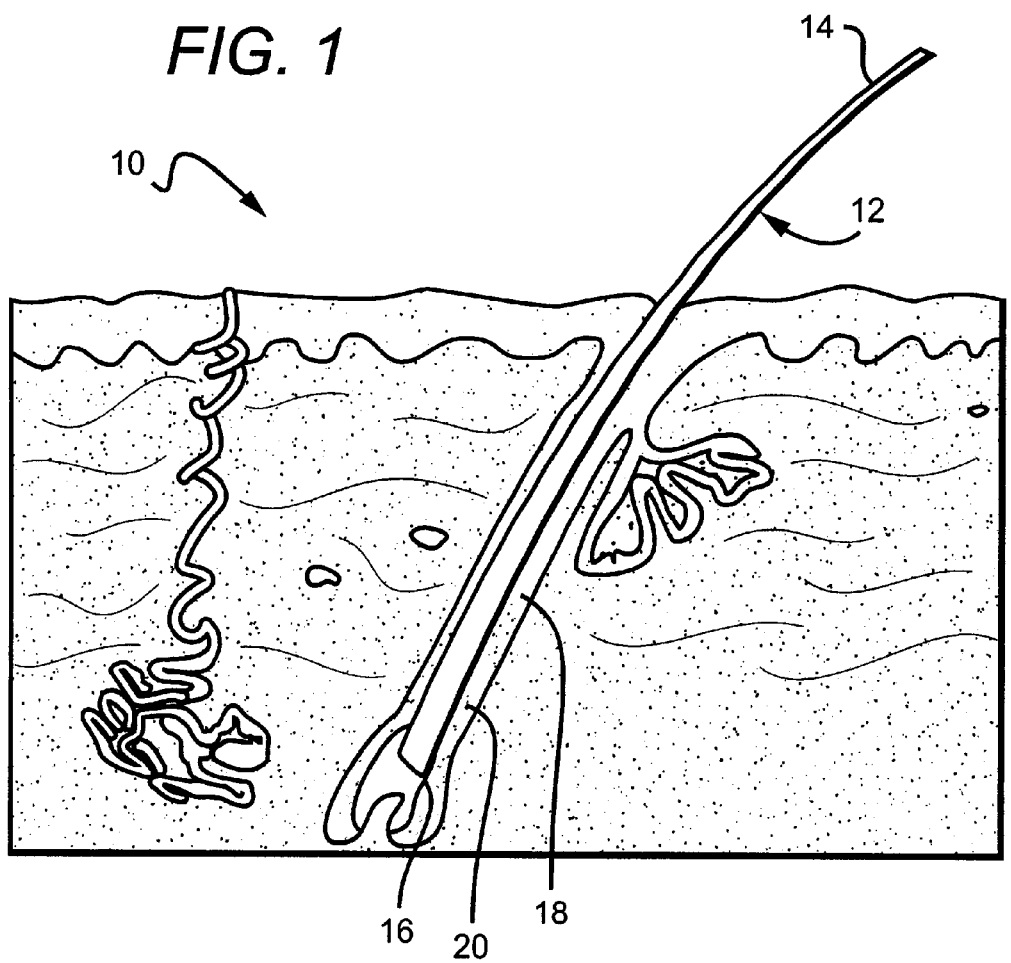
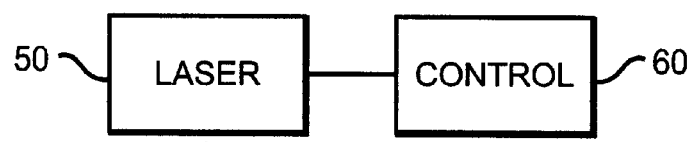
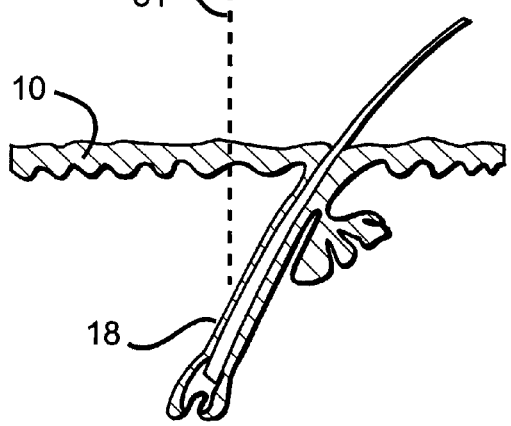
FIG. 2

DEPILATION

This application is a continuation-in-part of U.S. Ser. No. 08/972,416, which is a continuation-in-part of International (PCT) application No. GB94/02682 filed Dec. 7, 1994 designating the United States, and claiming priority from GB 9325109.8 filed Dec. 8, 1993.

BACKGROUND OF THE INVENTION

1. Field of the Invention

The present invention relates to a method of depilation of mammalian hair and also apparatus for use in the method.

2. State of the Art

The use of lasers in medical applications has been studied extensively since the early 1960's, particularly in relation to dermatology and ophthalmology. Biological tissue incorporates numerous cellular layers and different types of pigments, which respond in different ways to different types of radiation applied to the tissue. Therefore the type of laser selected for use in a particular biological application depends largely on the type of tissue to which the laser is to be applied and the nature of the effect required. Laser interactions fall generally into three distinct regimes, namely those producing photochemical, photothermal and photoionising effects. Each of these effects are caused by distinct ranges of laser parameters, such as, for example, different radiation dosages or different interaction times.

Photochemical effects are generally induced at low power output levels, and long interaction times. In contrast, the photoionising effects are generally produced with extremely high power dosages and short interaction times, usually leading to decomposition of irradiated biological material.

The use of lasers in depilation processes has been disclosed previously. For example, U.S. Pat. Nos. 3,538,919 and 4,617,926 are both concerned with depilation. These patents teach the stepwise irradiation of single hairs or hair follicles. The process described in U.S. Pat. No 3,538,919 involves inserting a laser probe within a hair follicle. The process described in U.S. Pat. No. 4,617,926 involves inserting a single hair within a bore of a fibre optic probe. These processes are time consuming, and can lead to unnecessary discomfort to a patient.

U.S. Pat. No. 5,059,192 to Zaias teaches a method of depilation using a Q-switched ruby laser, in which the laser wavelength is matched with the absorption spectrum of melanin found at the base of a hair follicle. Suitable selection of the laser parameters causes vaporization of the melanin via a single burst of energy, and thereby destruction of the selected hair follicle. Q-switched ruby lasers operate at very high power outputs for short pulse durations. A significant disadvantage in using such lasers is therefore that the apparatus cannot be used by substantially unskilled personnel because such high power is required. Such laser apparatus is therefore not suitable for cosmetic hair removal treatments. Furthermore, because Q-switched lasers operate in bursts or pulses of extremely short duration, many such bursts may be needed to cover an area of hair growth. This can be very time consuming, so that the method is not generally suitable for removing large areas of hair.

Furthermore, the use of pulsed Q-switched lasers in treatments for eradication of tattoos is known. It is well known that the irradiation of skin in this way, using Q-switched lasers, permits regrowth of hair.

It has been previously thought that the papilla was the source of life in hair and therefore that the destruction of the papilla would prevent regeneration and subsequent growth of the hair. However, it is now generally accepted that the cells in the region known as the bulge of the hair follicle in the dermis of the skin are primarily responsible for hair growth.

The dosage of laser radiation applied in the method of Zaias to destroy the papilla is between 0.4 to 10 J/cm$^2$ in a 30–40 nanosecond pulse. This dosage is within the photo-ionisation regime. Such conditions are not applicable to destruction of cells of the bulge region of hair follicle which is situated in the dermis of the skin closer to the skin surface (and not in the subcutis layer, where the papillae are located to be destroyed by the method of Zaias).

SUMMARY OF THE INVENTION

It is therefore an object of the present invention to provide a method of depilation using laser radiation in the photothermal range.

Another object of the invention is to provide a method of depilation which is simple to administer and can be used by non-medical personnel.

It is a further object of the invention to provide methods and apparatus for alleviating the problems in the art.

According to the present invention, a method is provided of depilation of mammalian hair. The method preferably utilizes a free-running laser having a power output in the photothermal range, which can be used in cosmetic treatment by relatively unskilled personnel, and which is highly effective in destroying the bulge area of cells in the hair follicle and therefore in a long-term removal of hair. The method of depilation generally comprises: (a) providing a laser source capable of emitting pulsed radiation, each pulse having a duration of 1 microsecond to 1 millisecond, said radiation having a wavelength in the range of 600 to 1500 nanometers; (b) selecting a treatment area of a subject's skin to be irradiated by said pulsed radiation, said treatment area including a plurality of irradiation zones; and (c) successively pulsing said laser source so as to irradiate successive zones of said treatment area with said radiation, and thereby destroy dermal biological material associated with hair growth. According to a preferred embodiment, the pulses are selectively provided with a duration in the range of 200 to 1000 microseconds, and each laser pulse provides a selected radiation exposure dose in the range of 2 to 25 J/cm$^2$.

According to other preferred aspects of the invention, the laser source preferably comprises either a ruby laser (wavelength 694.3 nm), a neodymium YAG laser (wavelength 1.064 μm), or other lasers having a wavelength in the 600 to 1500 nm (visible red to near infra-red) range. The selection of a laser having a wavelength in the range of 600 to 1500 nm is advantageous in that radiation in this wavelength range is capable of selectively destroying cells or other subdermal biological material responsible for hair growth, whilst not being substantially absorbed by surrounding cells or tissue.

It is preferred that a laser source with variable pulse duration is used. This is advantageous in facilitating irradiation of selected intensity, depending on the required application of the laser.

Advantageously, the irradiation zones are juxtaposed so as to substantially cover the treatment area of skin tissue. In one embodiment, the irradiation is controlled such that successive zones of the treatment area are irradiated by impinging successive pulses on different points on the treatment area in a boustrophedon manner. In any event, the irradiation is preferably controlled to ensure substantially complete irradiation of the treated area of skin tissue.

The irradiation generally destroys cells present at the bulge of individual hair follicles. The irradiation may further destroy cells present in the respective root regions of follicles.

There is further provided by the present invention depilation apparatus for use in a method as described above, the apparatus comprising: (a) a laser source capable of emitting pulsed radiation having a wavelength in the range of 600 to 1500 nm, wherein each pulse has a duration of 1 microsecond to 1 millisecond; and (b) means for controlling the laser so as to irradiate a zone of an individual's skin with the radiation, so as to be capable of selectively destroying biological material associated with hair growth present in the irradiation zone. According to a presently preferred embodiment, the pulse duration is selectively chosen between 200 and 1000 microseconds and each laser pulse provides a selected radiation exposure dose in the range of 2 to 25 $J/cm^2$ (and more preferably 5 to 25 $J/cm^2$).

The means for controlling the laser may further comprise means for effecting irradiation of successive zones of the skin tissue. Such means are typically arranged to provide movement of the irradiated beam and/or the apparatus relative to the subject's skin, so as to irradiate the skin tissue in a substantially boustrophedon manner substantially as described above.

Additional objects and advantages of the invention will become apparent to those skilled in the art upon reference to the detailed description taken in conjunction with the figures.

BRIEF DESCRIPTION OF THE DRAWINGS

FIG. 1 is a cross-section of a skin tissue region of a mammilian subject.

FIG. 2 is a block diagram of the apparatus of the invention in use.

DETAILED DESCRIPTION OF THE PREFERRED EMBODIMENTS

Referring to FIG. 1, there is illustrated a cross-section of the skin tissue region 10, showing a hair (generally designated 12) passing through the tissue region and protruding therefrom. The hair 12 has a shaft 14 extending to the follicle 16. The bulge region 18 of the hair follicle is in the dermal layer of the skin tissue region and is substantially distal from the papilla 20 (the latter being located in the subcutis layer). Destruction of the bulge region in a method according to the present invention will generally result in inhibition of hair re-growth.

Referring to FIG. 2, there is illustrated a laser source 50 provided with control means 60 for scanning the irradiated surface; i.e., for effecting irradiation of successive zones of the patient's skin tissue. Such means are typically arranged to provide movement of the irradiated beam and/or the apparatus relative to the subject's skin, so as to irradiate the skin tissue in a substantially boustrophedon manner. A pulsed beam 51 from the laser source 50 is directed at the skin tissue region 10 of the subject to be depilated. The beam impinges below the skin at the bulge region 18.

According to the invention, the laser source comprises either a ruby laser (wavelength 694.3 nm), a neodymium YAG laser (wavelength 1.064 $\mu$m), or another laser having a wavelength in the 600 to 1500 nm (visible red to near infra-red) range. The selection of a laser having a wavelength in the range of 600 to 1500 nm is advantageous in that radiation in this wavelength range is capable of selectively destroying cells or other subdermal biological material responsible for hair growth, whilst not being substantially absorbed by surrounding cells or tissue. According to the invention, the control means 60 causes the laser to be pulsed with a duration of 1 microsecond to 1 millisecond, and preferably with a duration of 200 to 1000 microseconds, and each laser pulse provides a radiation exposure dose preferably in the range of 2 to 25 $J/cm^2$, and more preferably in the range of 5 to 25 $J/cm^2$.

It is preferred that the laser source 50 be capable of variable pulse durations. This is advantageous in facilitation irradiation of selected intensity, depending on the required application of the laser.

According to the presently preferred embodiment, a variable pulse duration ruby laser having a wavelength of approximately 694 nm is utilized to achieve the depth of penetration required to destroy the bulge area of the follicle. The laser is preferably applied at a dose of 5 to 25 $J/cm^2$, typically in a substantially boustrophedon manner to the skin, in a manner such that the whole of the treatment area can be irradiated.

More particularly, and advantageously, the irradiation zones are juxtaposed so as to substantially cover the treatment area of skin tissue. It is preferred to control the irradiation such that successive zones of the treatment area are irradiated by impinging successive pulses on different points on the treatment area, typically in a boustrophedon manner. The method preferably ensures substantially complete irradiation of the treated area of skin tissue.

The irradiation generally destroys cells present at the bulge of individual hair follicles. The irradiation may further destroy cells present in the respective root regions of follicles.

There have been described and illustrated herein embodiments of a method and apparatus for depilation. While particular embodiments of the invention have been described, it is not intended that the invention be limited thereto, as it is intended that the invention be as broad in scope as the art will allow and that the specification be read likewise. It will therefore be appreciated by those skilled in the art that modifications could be made to the provided invention without deviating from its spirit and scope as so claimed.

We claim:

1. A method of depilation of hair from the skin of a mammalian subject, comprising:
    a) providing a laser source capable of emitting pulsed radiation having a wavelength between 600 and 1500 nm;
    b) selecting a treatment area of the subject's skin to be irradiated by said pulsed radiation, said treatment area including a plurality of juxtaposed irradiation zones; and
    c) pulsing said laser source, each pulse having a pulse duration in the range of 1 microsecond to 1 millisecond, so as to irradiate successive of said plurality of irradiation zones with said radiation, and thereby destroy subdermal biological material associated with hair growth.

2. A method according to claim 1, wherein:
said pulse duration is in the range of 200 microseconds to 1 millisecond.

3. A method according to claim 2, wherein:
said laser source comprises a ruby laser having a wavelength of 694.3 nanometers or a neodymium YAG laser having a wavelength of 1.064 micrometers, and said pulsing comprises generating a radiation exposure dose per pulse in a range of 2 to 25 J/cm$^2$.

4. A method according to claim 3, wherein:

said pulsing comprises successively pulsing in a boustrophedon manner so as to ensure substantially complete irradiation of said treatment area.

5. A method according to claim 1, wherein:

said laser source comprises a ruby laser having a wavelength of 694.3 nanometers or a neodymium YAG laser having a wavelength of 1.064 micrometers.

6. A method according to claim 1, wherein:

said pulsing comprises successively pulsing in a boustrophedon manner so as to ensure substantially complete irradiation of said treatment area.

7. A method according to claim 1, wherein:

said pulsing comprises generating a radiation exposure dose per pulse in a range of 2 to 25 J/cm$^2$.

8. An apparatus for effecting the depilation of a subject's skin, comprising:

a) a laser source means for emitting pulsed radiation having a duration of between 1 microsecond to 1 millisecond and having a wavelength between 600 and 1500 nanometers; and b) a laser control means coupled to said laser source means, said laser control means for controlling said laser source means so as to irradiate a plurality of juxtaposed irradiation zones of the subject's skin with said radiation and thereby selectively destroying biological material associated with hair growth present in said zone.

9. An apparatus according to claim 8, wherein:

said duration is between 200 microseconds and 1 millisecond.

10. An apparatus according to claim 8, wherein:

said laser control means is arranged to control said laser source means to pulse at any of a plurality of preselected durations between 1 microsecond and 1 millisecond.

11. An apparatus according to claim 8, wherein:

said laser control means effects irradiation of successive zones of the subject's skin.

12. An apparatus according to claim 11, wherein:

said laser control means comprises means for effecting movement of said apparatus relative to the patient's skin so as to irradiate said successive zones, said successive zones being juxtaposed.

13. An apparatus according to claim 12, wherein:

said means for effecting movement irradiates said plurality of juxtaposed irradiation zones in a boustrophedon manner.

14. An apparatus according to claim 8, wherein:

said laser source means comprises a ruby laser having a wavelength of 694.3 nanometers or a neodymium YAG laser having a wavelength of 1.064 micrometers.

15. An apparatus according to claim 8, wherein:

said laser control means comprises means for causing said laser source means to provide pulses having radiation exposure doses in a range of 2 to 25 J/cm$^2$.

16. An apparatus according to claim 15, wherein:

said laser source means comprises a ruby laser having a wavelength of 694.3 nanometers or a neodymium YAG laser having a wavelength of 1.064 micrometers, and said duration is between 200 microseconds and 1 millisecond.

17. An apparatus according to claim 16, wherein:

said laser control means is arranged to control said laser source means to pulse at any of a plurality of preselected durations between 200 microsecond and 1 millisecond.

* * * * *